US00PP07897P

United States Patent [19]

Winner

[11] Patent Number: Plant 7,897

[45] Date of Patent: Jun. 30, 1992

[54] VARIETY OF GERANIUM NAMED RITZ

[75] Inventor: Blair L. Winner, Lompoc, Calif.

[73] Assignee: Denholm Seeds, Inc., Lompoc, Calif.

[21] Appl. No.: 639,206

[22] Filed: Jan. 9, 1991

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 5,054 5/1983 Elsner ..... Plt. 68

P.P. 6,064 12/1987 Winner ..... Plt. 68

*Primary Examiner*—James R. Feyrer

*Attorney, Agent, or Firm*—Webb, Burden, Ziesenheim & Webb

[57] ABSTRACT

The new cultivar is characterized by the compactness and height of its velvet appearing, deep orange-red flowers 5.0 to 7.5 cm. above the leaves. The variety has been trialed outdoors and shows good heat tolerance, resistance to wind and rain, and continual flowering.

1 Drawing Sheet

BACKGROUND OF THE INVENTION

The present invention comprises a new and distinct cultivar of *Pelargonium*×*hortorum* known by the varietal name Ritz (Oglevee No. 7088, Denholm Code 81113-3). The new variety was discovered in a selected breeding program in 1981 at Denholm Seeds in Lompoc, Calif. The new variety is a selection from the crossing of Victoria (U.S. Plant Pat. No. 6,064) and Veronica (U.S. Plant Pat. No. 5,054).

Ritz is similar to Victoria in total plant and flower height. The new cultivar has similar color range, petal and petaloid count, good heat tolerance, and continual flowering as that of Victoria. The similarities between Ritz and Veronica are that both plants are dwarf, have good heat tolerance, and are resistant to wind and rain. Ritz differs from Victoria in that it has a slightly darker color tint with a Red group 53D eye and the flowers are 5.0 to 7.5 cm. above the leaves rather than close to the leaves. Ritz is overall a taller plant than Veronica, and the flower color is more in the scarlet range than that of Veronica.

The new variety was first asexually reproduced by cuttings at Denholm Seeds, Lompoc, Calif. 93436. The new variety has been asexually reproduced by cuttings at Oglevee Ltd. in Connellsville, Pa. over a several-year period. It has also been trial and field tested at Connellsville, Pa. and has been found to retain its distinctive characteristics through successive propagations.

The cultivar, when grown in a glass greenhouse in Connellsville, Pa. using natural light and 60° F. night, 68° F. day and 71° F. vent, has a response time of six weeks from rooted cutting to flowering in a 10 cm. pot. The response time was determined on plants grown in soilless media employing constant fertilizer of 200 parts per million of nitrogen and potassium in full light. The rooted cuttings were potted Feb. 14, 1990 and flowered on Apr. 1, 1990.

DESCRIPTION OF THE DRAWING

FIG. 1 of the accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Pa. The plant history was taken on six-week plants blossomed under natural light in a greenhouse, and the color readings were taken indoors under 150–175 foot candles of florescent cool white light. Color references are primarily to the RHS Colour Chart of The Royal Horticultural Society of London.

THE PLANT

Classification:

*Botanical.*—*Pelargonium*×*hortorum.*

*Commercial.*—Zonal Geranium.

Form: Upright compact habit, basal branching.

*Height.*—21.0 to 24.0 cm. above media surface.

*Growth.*—Free and early flowering, basal branching, compact mound habit.

Strength: Very sturdy, resistant to wind and rain damage.

Foliage: Little or no zoning; stalked leaf attachment.

Leaves:

*Size.*—7.0 to 9.5 cm. across.

*Shape.*—Reniform; cordate base.

*Margin.*—Crenate.

*Texture.*—Pubescent; slightly reflective.

*Color.*—Top: Green group 137A. Bottom: Yellow/green group 146B.

*Ribs and veins.*—Palmate venation. Color: Yellow/green group 147C.

Petioles:

*Color.*—Green group 137C.

*Length.*—7.0 to 10.5 cm.

Stem:

*Color.*—Yellow/green group 146B.

*Internodes.*—1.5 to 2.5 cm.

THE BUD

Shape: Upright, hemispherical cluster.

Size: 2.5 to 3.5 cm. across.

INFLORESCENCE

Blooming habit: Hemispherical, upright, semi-double; continuous blooming.

Size: 10.0 to 11.0 cm. across.

Borne: Umbel; florets on pedicel, pedicel on peduncle; 5.0 to 7.5 cm. above foliage canopy.

Florets:

*Form.*—Flat to slightly cupped.

*Color.*—Top: Red group 42A with an eye on upper two petals of Red group 53D. Bottom: Red group 44C.

*Petals.*—Obovate; separate, not united; margin entire, 5 to 7 in number.

*Size.*—4.0 to 5.0 cm. across.

*Texture and appearance.*—Smooth, satiny; appearance from a distance is a deep orange-red color with a velvet like appearance above a compact mound of medium green foliage.

Petaloids:

*Quantity.*—0–3 in number.

*Shape.*—Narrow, elongated, twisted, some petal-like with pollen attached.

*Color.*—Top: Red group 42A. Bottom: Red group 44C.

Pedicel:

*Length.*—3.0 to 4.5 cm.

*Color.*—Yellow/green group 146C.

Peduncle: Arises from the node opposite the leaf petiole.

*Length.*—11.5 to 16.0 cm.

*Color.*—Yellow/green group 146B.

Disease resistance: Not known.

Lasting quality: Holds up well under the stress of heat, wind and rain.

REPRODUCTIVE ORGANS

Stamens:

*Anthers.*—2.0–3.0 mm. in length.

*Filaments.*—Irregular shape. Color: White at base to pink at anther end. Length: 7.0 to 8.0 mm.

*Pollen.*—Golden brown.

Pistils:

*Number.*—One.

*Length.*—9.0 to 10.0 mm.

*Stigma.*—One, 5 or 6 parted; pink.

*Style.*—3.0 to 4.0 mm. in length; pink in color.

Ovaries: Superior; pale green, pubescent; 5.0 mm. in length.

Fruit: Few observed.

GENERAL CHARACTERISTICS

This new and distinct cultivar is characterized by its compactness, improved cutting production and exceptional outdoor performance.

The deep orange-red bloom and the outdoor performance is a welcome addition to the color class which includes the current varieties Kim (U.S. Plant Pat. No. 5,311) and Crimson Fire (unpatented).

I claim:

1. A new and distinct variety of geranium plant substantially as shown and described.

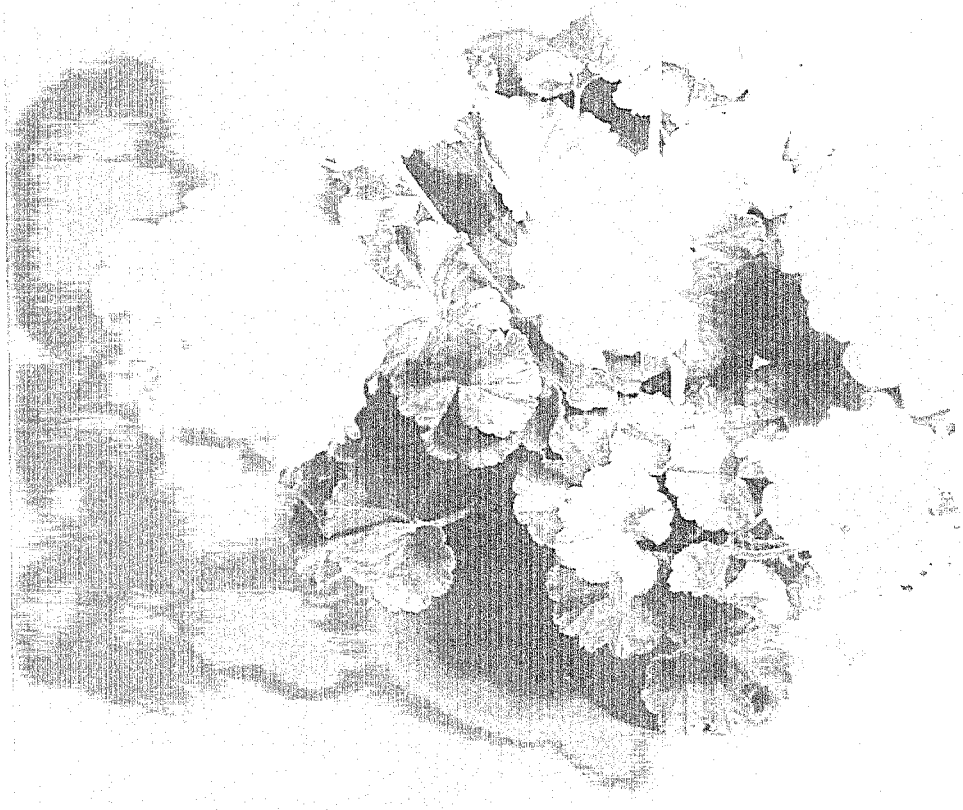

* * * * *